US010413243B2

(12) United States Patent
Burkett et al.

(10) Patent No.: US 10,413,243 B2
(45) Date of Patent: Sep. 17, 2019

(54) INTRAVASCULAR DEVICES, SYSTEMS, AND METHODS HAVING AN ADHESIVE FILLED FLEXIBLE ELEMENT

(71) Applicant: Volcano Corporation, San Diego, CA (US)

(72) Inventors: David H. Burkett, Temecula, CA (US); Eric Henderson, Temecula, CA (US); Chris Szunyog, Murrieta, CA (US); Ramiro Reyes, Oceanside, CA (US)

(73) Assignee: VOLCANO CORPORATION, San Diego, CA (US)

( * ) Notice: Subject to any disclaimer, the term of this patent is extended or adjusted under 35 U.S.C. 154(b) by 720 days.

(21) Appl. No.: 14/837,611

(22) Filed: Aug. 27, 2015

(65) Prior Publication Data

US 2016/0058382 A1 Mar. 3, 2016

Related U.S. Application Data

(60) Provisional application No. 62/043,115, filed on Aug. 28, 2014.

(51) Int. Cl.
*A61B 5/02* (2006.01)
*A61B 5/00* (2006.01)
(Continued)

(52) U.S. Cl.
CPC ............ *A61B 5/6851* (2013.01); *A61B 5/026* (2013.01); *A61B 5/0215* (2013.01); *A61B 18/1492* (2013.01); *A61B 6/12* (2013.01); *A61B 6/487* (2013.01); *A61B 8/0891* (2013.01); *A61B 8/12* (2013.01); *A61B 2018/00791* (2013.01);
(Continued)

(58) Field of Classification Search
CPC ......... A61B 5/00; A61B 5/0215; A61B 5/026; A61B 5/6851; A61B 18/1492; A61B 2562/12; A61B 8/0891; A61B 8/12; A61B 2018/00791; A61B 2090/064; A61B 2090/396; A61M 2025/09166; A61M 2025/09133; A61M 2025/09108; A61M 2025/09083; A61M 2205/3344; A61M 2205/3334; A61M 2210/12
See application file for complete search history.

(56) References Cited

U.S. PATENT DOCUMENTS

| 5,125,137 A | 6/1992 | Corl et al. |
| 5,147,317 A | 9/1992 | Shank et al. |
| 5,542,434 A * | 8/1996 | Imran ............... A61M 25/0144 600/585 |
| 5,873,835 A | 2/1999 | Hastings et al. |

(Continued)

FOREIGN PATENT DOCUMENTS

EP 0998323 A1 5/2000

*Primary Examiner* — Eric J Messersmith

(57) ABSTRACT

Intravascular devices, systems, and methods are disclosed. In some instances, the intravascular device is a guide wire with an adhesive filled flexible element. For example, in some implementations a sensing guide wire includes a flexible elongate member; a flexible element extending distally from the flexible elongate member; a core member extending within a lumen of the flexible element; at least one flexible adhesive filling at least a portion of the lumen between the core member and the flexible element along a length of the flexible element; and a sensing element positioned distal of the flexible element. Methods of making, manufacturing, and/or assembling such intravascular devices and associated systems are also provided.

17 Claims, 13 Drawing Sheets

(51) Int. Cl.
*A61B 5/0215* (2006.01)
*A61B 5/026* (2006.01)
*A61B 18/14* (2006.01)
*A61M 25/09* (2006.01)
*A61B 6/12* (2006.01)
*A61B 6/00* (2006.01)
*A61B 8/08* (2006.01)
*A61B 8/12* (2006.01)
*A61B 18/00* (2006.01)
*A61B 90/00* (2016.01)

(52) U.S. Cl.
CPC . *A61B 2090/064* (2016.02); *A61B 2090/3966* (2016.02); *A61B 2562/12* (2013.01); *A61M 2025/09083* (2013.01); *A61M 2025/09108* (2013.01); *A61M 2025/09133* (2013.01); *A61M 2025/09166* (2013.01); *A61M 2205/3334* (2013.01); *A61M 2205/3344* (2013.01); *A61M 2210/12* (2013.01)

(56) References Cited

U.S. PATENT DOCUMENTS

| | | | |
|---|---|---|---|
| 6,106,476 | A | 8/2000 | Corl |
| 6,464,684 | B1 | 10/2002 | Galdonik |
| 6,551,250 | B2 | 4/2003 | Khalil et al. |
| 2003/0065316 | A1* | 4/2003 | Levine .................. A61B 18/26 606/33 |
| 2012/0004493 | A1 | 1/2012 | Hedger et al. |
| 2014/0005543 | A1 | 1/2014 | Burkett et al. |
| 2014/0005561 | A1 | 1/2014 | Burkett |
| 2014/0058251 | A1 | 2/2014 | Stigall et al. |
| 2014/0058257 | A1* | 2/2014 | Stigall .................. A61B 19/54 600/431 |
| 2014/0066790 | A1* | 3/2014 | Burkett ................ A61M 25/09 600/486 |
| 2014/0180141 | A1 | 6/2014 | Millett et al. |
| 2014/0187874 | A1 | 7/2014 | Burkett et al. |
| 2014/0187980 | A1 | 7/2014 | Burkett et al. |
| 2014/0187984 | A1 | 7/2014 | Burkett et al. |
| 2015/0217090 | A1 | 8/2015 | Burkett et al. |

* cited by examiner

INTRAVASCULAR DEVICES, SYSTEMS, AND METHODS HAVING AN ADHESIVE FILLED FLEXIBLE ELEMENT

CROSS REFERENCE TO RELATED APPLICATIONS

The present application claims priority to and the benefit of the U.S. Provisional Patent Application No. 62/043,115, filed Aug. 28, 2014, which is hereby incorporated by reference in its entirety.

TECHNICAL FIELD

The present disclosure relates to intravascular devices, systems, and methods. In some embodiments, the intravascular devices are guide wires that include a distal coil filled with a flexible adhesive.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire.

Further, a problem with existing pressure and flow guide wires is that the coil(s) defining the distal tip of the device can be fragile and prone to unwanted bending or kinking. In that regard, the small diameter and high flexibility of the coil(s) limits the structural integrity that can be provided. Further, the rigid nature of the sensor housing adjacent to the coil(s) causes additional stress to be applied to the coil(s) during use, especially when traversing complex vasculature with many curves and turns. As a result, the handling and performance of the guide wires can be reduced because of the limitations of the coil(s).

Guide wires are designed to be steered through vascular anatomy to suspected lesion sites to allow for treatment of those lesions. There are many desired performance characteristics that have to be considered for the guide wire design: torqueability, support level, tip stiffness, lubricity, smooth transitions, and device compatibility. Regardless of the design needs, good torqueability of the wire tip remains the most important performance output of the wire. Without good torque control of the tip of the wire, physicians have difficulty steering the tip into the appropriate branches to reach the desired lesion.

In order to make a guide wire that meets the desired output requirement, a flexible section of the guide wire (typically the distal most 20 to 40 cm of the wire that will be inserted into the vasculature) can be created via grinding of the core wire to create the desired support and transition conditions. To improve compatibility with other devices that will be advanced over the guide wire, a covering is often placed over the ground section of the core wire and coated with a lubricious coating to improve lubricity. Flexible coverings can include one or more coils, tubes, and/or tubes with integrated spiral coil support. The flexible coverings can be aligned to adjacent components of the guide wire and locked into place at each end via adhesive or solder. These types of flexible coverings are typically attached to the core wire in only two places, at the proximal and distal ends of the flexible covering. In that regard, a rigid adhesive is often used to fixedly secure the ends of the flexible covering to the core wire. The lubricious coatings that are applied to these coverings provide excellent movement in an axial direction within the vasculature and also help devices move smoothly over the wire. However, the traditional use of flexible coverings has a significant deficiency relating to torqueing the tip of the guide wire when the distal section of the guide wire, including the flexible covering, is in tortuosity. In that regard, the more tortuosity that the flexible covering is pushed into and/or the more acute the tortuosity becomes, the more the torqueability of the guide wire tip is degraded.

This degradation in torqueability of the distal section of the guide wire relative to the proximal section of the guide wire occurs because the flexible coverings have very poor torqueability characteristics. For example, when the distal section of the guide wire is in significant tortuosity, as the proximal end of the wire is rotated, the torque is poorly transmitted to the from the core wire to the flexible covering because the flexible covering is typically only attached at each end. This results in the guide wire building up torque with the tip rotation lagging behind the proximal rotation. When the flexible covering is only locked at its ends, the core wire is rotating against a non-lubricious inner surface of the flexible covering and, therefore, not getting the benefit of the lubricity of the outer coating of the flexible covering. At some point, the torque builds up enough to overcome the tortuosity effect on the flexible covering and the flexible covering suddenly spins causing the distal tip of the guide wire to whip through a large angle quickly. This whipping of the distal tip worsens with severe tortuosity and/or increased length of tortuosity. The unwanted whipping of the distal tip can cause problems with placing the guide wire in the desired location within the patient's anatomy and, in severe cases, can even cause damage to the patient's anatomy.

Accordingly, there remains a need for intravascular devices, systems, and methods that include one or more electronic, optical, or electro-optical components and have improved handling characteristics.

SUMMARY

The present disclosure is directed to intravascular devices, systems, and methods that include a guide wire having a distal flexible element at least partially filled with a flexible adhesive.

For example, in some instances, a flexible covering is secured to the core member with a low durometer adhesive within a distal section of the guide wire and along the full length, or at least a majority of the length, of the flexible covering. This approach provides a significant improvement in torqueability when the guide wire is in significant tortuosity. In that regard, by applying the adhesive along the full length, at least a majority of the length, and/or at spaced intervals along the length of the flexible covering, the torque transmission from the core member to the flexible covering is provided along the full length of the flexible covering and allows the lubricity of the outer surface of the flexible covering to improve torqueability of the guide wire within the vessel of the patient. Suitable flexible adhesives include those with a low to medium durometer (for example, between 25A and 60D, including 90A in some instances), good flexibility, reasonable shear strength, and low to medium viscosity prior to curing for ease of application within the flexible covering. Examples of suitable adhesives include, but are not limited to urethane adhesives and silicon adhesives, such as Dymax 1901-M, Dymax 9001, etc.

Beyond the advantage in torqueability improvement of the guide wire, there are a number of other benefits of using a flexible adhesive to secure the flexible cover to the core member along the entire length, or a majority of the length, of the flexible covering. For example, as the core tapers toward the tip, the impact of a harder adhesive would then begin to impact bending stiffness and thus potentially create other undesirable performance issues, such as kinking when the hard adhesive fractures in tight tortuosity. Also, when the guide wire is a pressure, flow, or other type of sensor-based guide wire with fragile electrical conductor wires, harder adhesives could damage the conductors when the adhesive fractures in tortuosity. Further locking the conductors of a sensor-based guide wire between the core and covering with a flexible adhesive can eliminate or greatly minimize potential conductor failure as the conductors can be stressed during the whipping effect. Further still, filling the flexible covering with adhesive may minimize damage to the flexible covering by providing internal support to the structure of the flexible covering that can minimize kinking of the flexible covering, minimize potential for stretching or bunching up (like a sock) of the flexible covering, and minimize potential for overlap of adjacent portions of the flexible covering (e.g., windings of a coil) to occur in very tight tortuosity.

In addition, flexible adhesives can also provide benefit in the use of radiopaque marker coils. For example, the flexible adhesive can be used to lock a marker coil that has been wound into a desired marker pattern in the desired orientation. For example, the pattern can alternate between stacked lengths and high-pitch windings to provide a radiopaque pattern for visualization of the distal tip of the guide wire under fluoroscopy. These markers can be useful in co-registration of a sensor-based guide wire to the x-ray images and can also have use for estimating lesion or other anatomical measurements. A single component coil wound into a desired pattern also has a major benefit in that it is easy to create desired variations in the marker pattern when winding the coil.

The use of flexible adhesives within the flexible elements of the distal portion of the guide wire can also be used for transition support in the distal portion of the wire. This can be important in sensor-based guide wires where stiff sensor housings may be used to mount and/or protect the sensors. Often such housings are placed at approximately 3 cm from the distal tip of the guide wire, with a radiopaque tip coil extending the 3 cm from the housing to the distal tip. Stiff sensor housings can cause kinking of the flexible core member just distal to the housing as the guide wire is being pushed into a tight vessel takeoff. In order to minimize adverse effects of the rigid sensor housing on the distal tip of the guide wire, the flexible adhesive can be applied to the proximal 1-2 cm of the tip coil, leaving the distal 1-2 cm free of adhesive and, thereby, providing a more gradual transition in support from the relatively rigid housing to the highly flexible radiopaque tip coil. This can allow a physician to shape the tip of the wire in a more traditional manner (i.e., as with a frontline guide wire that does not include a sensor) and does not require the tip to be designed even more flexible to compensate for the effect of the adhesive on the atraumatic tip.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
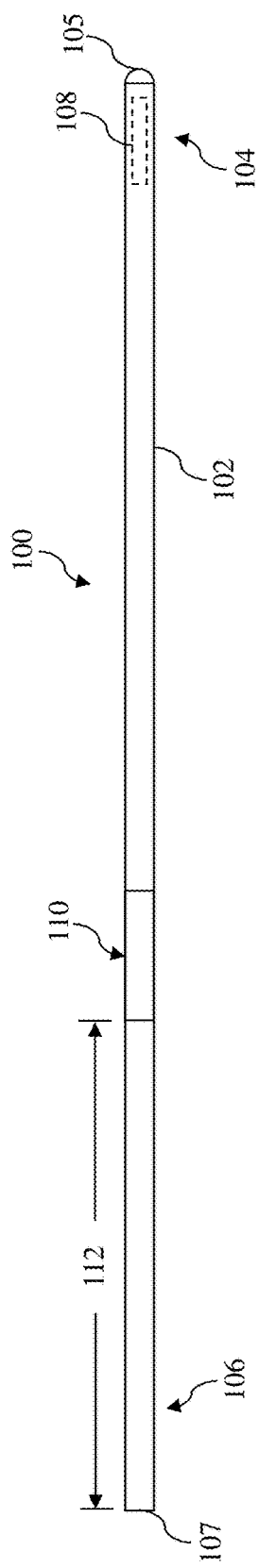
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a minor, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal tip 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a minor, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In some embodiments the electrical conductors are embedded within a core of the flexible elongate member. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Similarly, in some embodiments the optical fibers are embedded within a core of the flexible elongate member. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. In some instances, at least one of the electrical conductors and/or optical pathways is embedded within the core of the flexible elongate member 102, as described in U.S. Provisional Patent Application No. 61/935,113, filed Feb. 3, 2014, published as U.S. Patent Application Publication No. 2015/0217090 on Aug. 6, 2015, which is hereby incorporated by reference in its entirety. Generally, any number of electrical conductors, optical pathways, and/or combinations thereof can extend along the length of the flexible elongate member 102 between the connector 110 and the component 108, embedded in the core or not. In some instances, between one and ten electrical conductors and/or optical pathways extend along the length of the flexible elongate member 102 between the connector 110 and the component 108. The number of communication pathways and the number of electrical conductors and optical pathways extending along the length of the flexible elongate member 102 is determined by the desired functionality of the component 108 and the corresponding elements that define component 108 to provide such functionality.

Referring now to FIGS. 2-6, shown therein are aspects of the intravascular devices of the present disclosure that include one or more flexible elements filled with a flexible adhesive. In that regard, one of the major issues associated with existing functional guide wires is poor mechanical performance as compared to frontline guide wires. The use of an adhesive filled coil at the distal tip of the intravascular device and/or an adhesive filled flexible element proximal of the a sensing element in accordance with the present disclosure has been found to significantly improve the mechanical performance of the guide wires, including the durability of the distal assembly.

Figure 2:
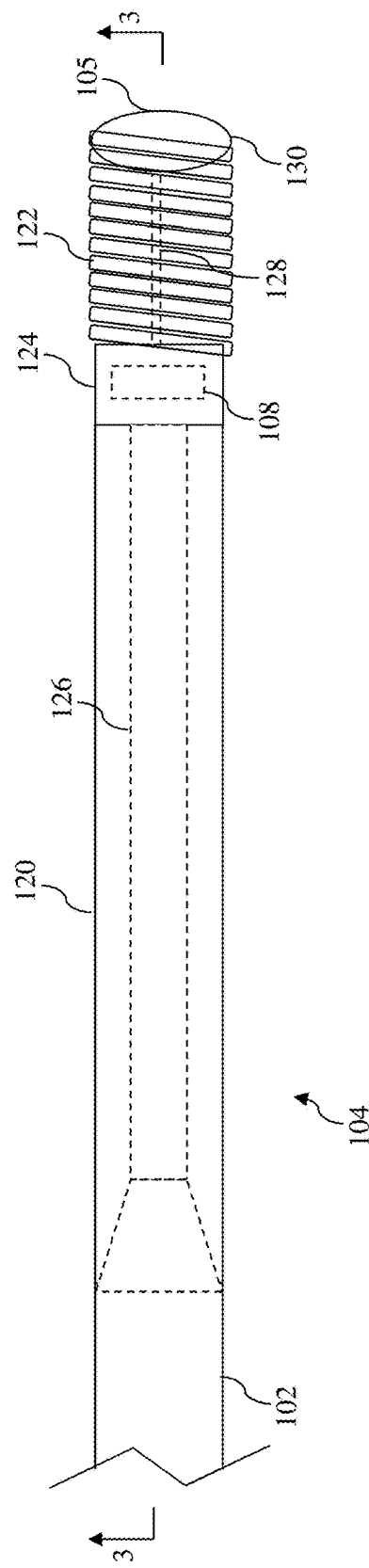
FIG. 2 is a diagrammatic, schematic side view of a distal portion of the intravascular device of FIG. 1 according to an embodiment of the present disclosure.

Referring now to FIG. 2, shown therein is a diagrammatic, schematic side view of the distal portion 104 of the intravascular device 100 according to an embodiment of the present disclosure. As shown, the distal portion 104 includes a proximal flexible element 120 and a distal flexible element 122 on each side of a housing 124 containing component 108. A core member 126 extends through the proximal flexible element 120. Similarly, a core member 128 extends through the distal flexible element 122. In some implementations, the core members 126 and 128 are an integral component (i.e., the core member 126 extends through the housing 124 and to define core member 128). Generally, the core members 126, 128 are sized, shaped, and/or formed out of particular material(s) to create a desired mechanical performance for the distal portion 104 of the intravascular device 100. In that regard, in some instances the core member 128 is coupled to a shaping ribbon. For example, in some particular implementations the core member 128 is coupled to a shaping ribbon utilizing a multi-flat transition as described in U.S. Provisional Patent Application No. 62/027,556, filed Jul. 22, 2014, which is hereby incorporated by reference in its entirety.

The proximal and distal flexible elements 120, 122 can be any suitable flexible element, including coils, polymer tubes, and/or coil-embedded polymer tubes. In the illustrated embodiment the proximal flexible element 120 is a coil-embedded polymer tube and the distal flexible element 122 is a coil. As discussed in greater detail below, the proximal and/or distal flexible elements 120, 122 are at least partially filled with one or more flexible adhesives to improve the mechanical performance and durability of the intravascular device 100. In that regard, in some instances adhesives with varying degrees of durometer are utilized to provide a desired transition in bending stiffness along the length of the intravascular device 100. A solder ball 130 or other suitable element is secured to the distal end of the distal flexible element 122. As shown, the solder ball 130 defines the distal tip 105 of the intravascular device 100 with an atraumatic tip suitable for advancement through patient vessels, such as vasculature. In some embodiments, a flow sensor is positioned at the distal tip 105 instead of the solder ball 130.

The distal portion 104 of the intravascular device 100—as well as the proximal portion 106 and the flexible elongate member 102—may be formed using any suitable approach so long as the distal flexible element 122 is filled with a flexible adhesive in accordance with the present disclosure. Accordingly, in some implementations the intravascular device 100 includes features similar to the distal, intermediate, and/or proximal sections described in one or more of U.S. Pat. Nos. 5,125,137, 5,873,835, 6,106,476, 6,551,250, U.S. patent application Ser. No. 13/931,052, filed Jun. 28, 2013, published as U.S. Patent Application Publication No. 2014/0005543 on Jan. 12, 2014, U.S. patent application Ser. No. 14/135,117, filed Dec. 19, 2013 published as U.S. Patent Application Publication No. 2014/0180141 on Jun. 26, 2014, U.S. patent application Ser. No. 14/137,364, filed Dec. 20, 2013 published as U.S. Patent Application Publication No. 2014/0187980 on Jul. 3, 2014, U.S. patent application Ser. No. 14/139,543, filed Dec. 23, 2013 published as U.S. Patent Application Publication No. 2014/0187984 on Jul. 3, 2014, U.S. patent application Ser. No. 14/143,304, filed Dec. 30, 2013 published as U.S. Patent Application Publication No. 2014/0187874 on Jul. 3, 2014, and U.S. Provisional Patent Application No. 61/935,113 filed Feb. 3, 2014 published as U.S. Patent Application Publication No. 2015/0217090 on Aug. 6, 2015, each of which is hereby incorporated by reference in its entirety.

Figure 3:
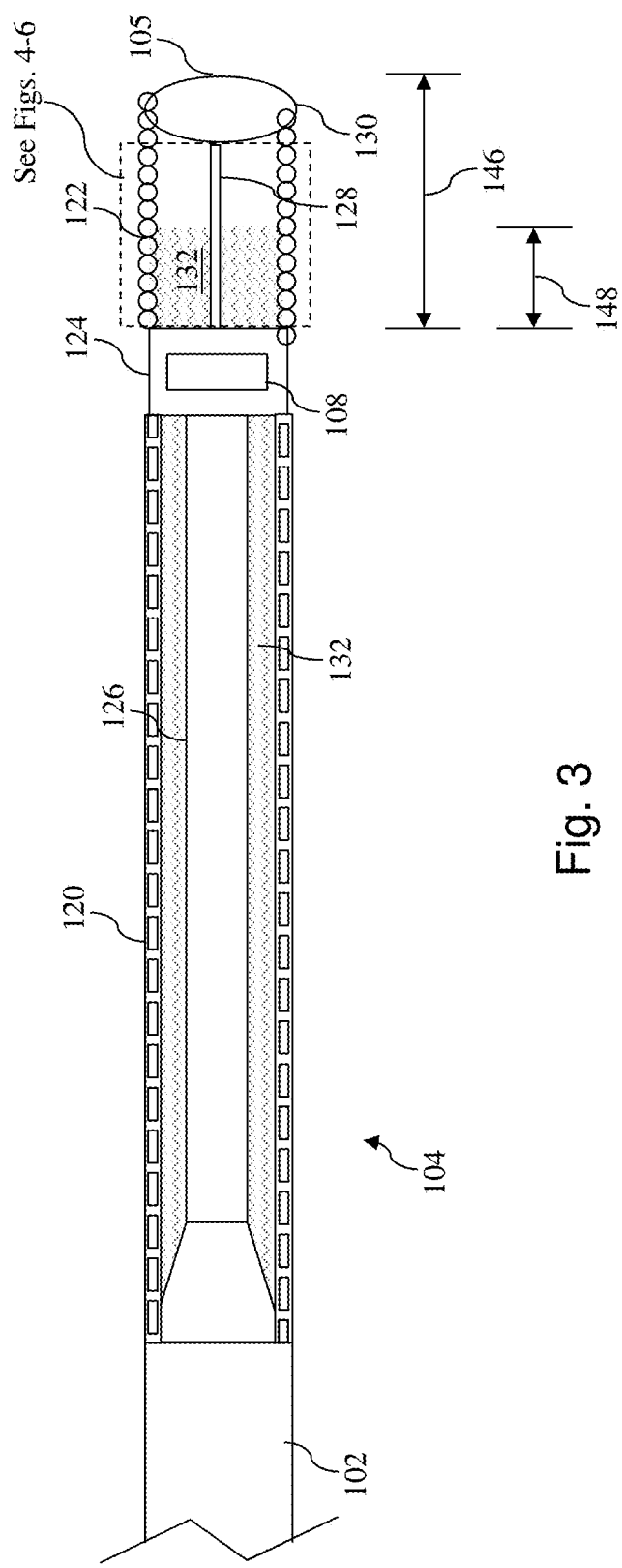
FIG. 3 is a cross-sectional side view of the distal portion of the intravascular device of FIGS. 1 and 2 taken along section line 3-3 of FIG. 2 according to an embodiment of the present disclosure.

Referring now to FIG. 3, shown therein is a cross-sectional side view of the distal portion 104 of the intravascular device 100 taken along section line 3-3 of FIG. 2 according to an embodiment of the present disclosure. As shown, the proximal and distal flexible elements 120, 122 are filled, or partially filled, with one or more flexible materials. In that regard, the material(s) filling, or partially filling, the flexible elements is (are) configured to improve the mechanical integrity of the proximal and distal flexible elements 120,122, while maintaining sufficient flexibility for use of the intravascular device in tortuous vessels. In some instances, the materials include one or more flexible adhesives, such as Dymax 1901-M, Dymax 9001, etc. In that regard, in some implementations the flexible adhesives have a minimum durometer of shore hardness 25A to a maximum durometer of shore hardness 60D.

As shown, in the illustrated embodiment a flexible adhesive 132 fills substantially all of the open space within the lumen of the flexible element 120. However, as will be discussed below, in other instances multiple flexible adhesives are utilized to fill, or partially fill, the interior of the flexible element 120. In that regard, the one or more flexible adhesives generally fill the space within the flexible element along the full length, or at least a majority of the length of the flexible element 120, including at least fifty percent, at least sixty percent, at least seventy percent, at least eighty percent, at least ninety percent, and at least ninety-nine percent of the length of the flexible element in some implementations. In some implementations, the flexible adhesive is introduced at spaced intervals, with fixed and/or variable spacing, along the length of the flexible covering. For example, openings can be created in the flexible element 120 at the spaced intervals to allow introduction of the flexible adhesive at different points along the length of the flexible element. The flexible adhesive(s) secure the flexible element 120 to the proximal core 126 along a majority of the length of the flexible element 120. Accordingly, the flexible element 120 is much less likely to slip or twist relative to the proximal core 126 compared to a typical design where the flexible element 120 is secured to the proximal core 126 only at the proximal and distal ends of the flexible element 120. As a result of the use of the flexible adhesive(s) along a majority of the length of the flexible element 120, the distal portion of the intravascular device 100 is more responsive to movements imparted at the proximal end of the intravascular device 100, providing improved handling and control to a user.

In the context of a coil distal flexible element 122, the flexible adhesive can secure the windings in place relative to one another, which helps protect the distal portion 104 of the intravascular device 100 from damage during subsequent manufacturing steps, transport, and/or use. In that regard, the adhesive(s) will lock the coil position relative to itself and the distal core 128. This can greatly minimize potential for damage to the tip due to stretching of the coils during handling or use. All tip coils need to have some initial stretch because a stacked coil would have significantly high column strength and could overlap coils when put into tortuosity. However, the more stretch in the coil, the more easily the coil can be damaged. Embodiments of the present disclosure help prevent this from happening.

Figure 4:
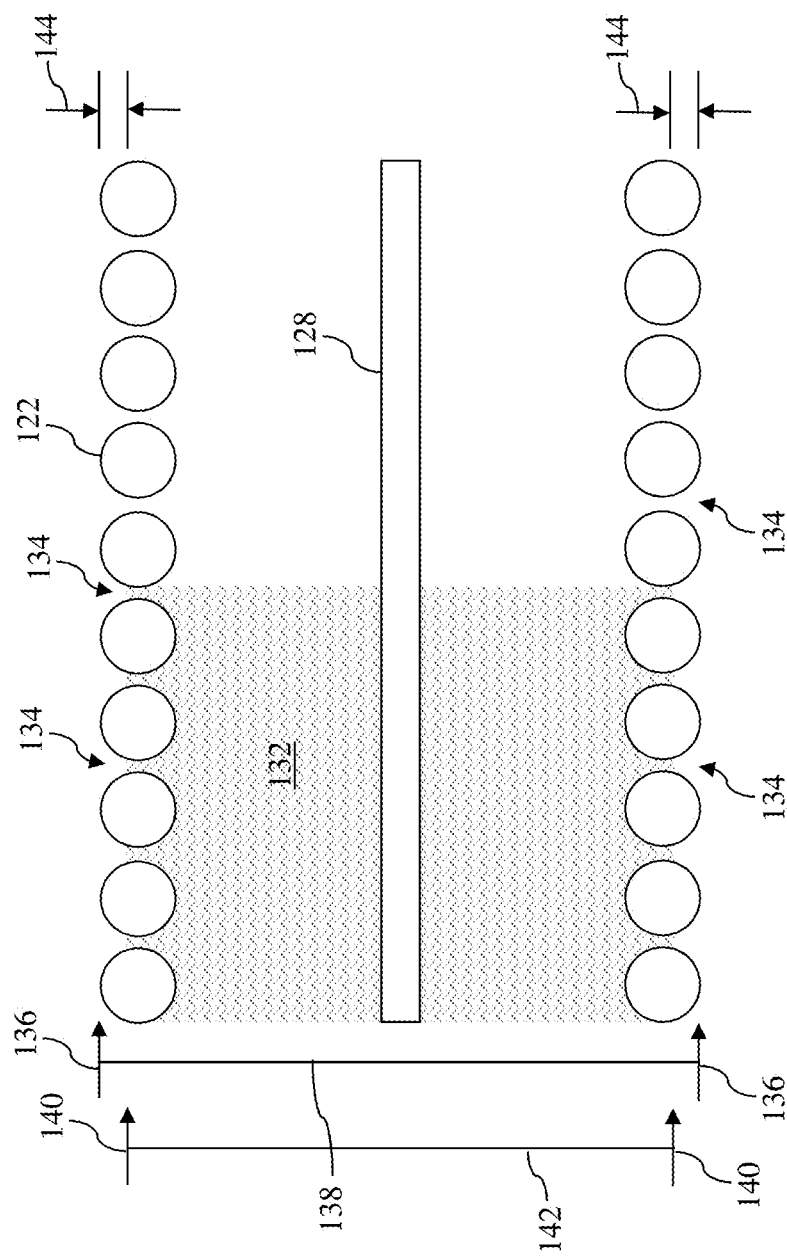
FIG. 4 is a magnified cross-sectional side view of a section of the distal portion of the intravascular device of FIGS. 1-3 according to an embodiment of the present disclosure.
Figure 5:
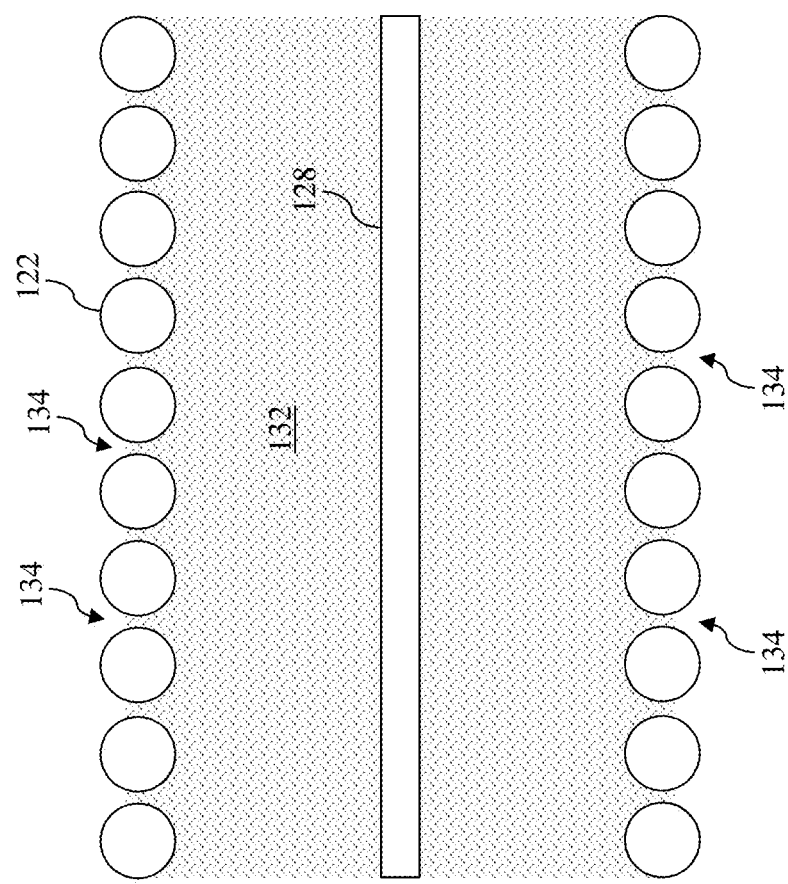
FIG. 5 is a magnified cross-sectional side view of a section of the distal portion of the intravascular device of FIGS. 1-3 according to another embodiment of the present disclosure.
Figure 6:
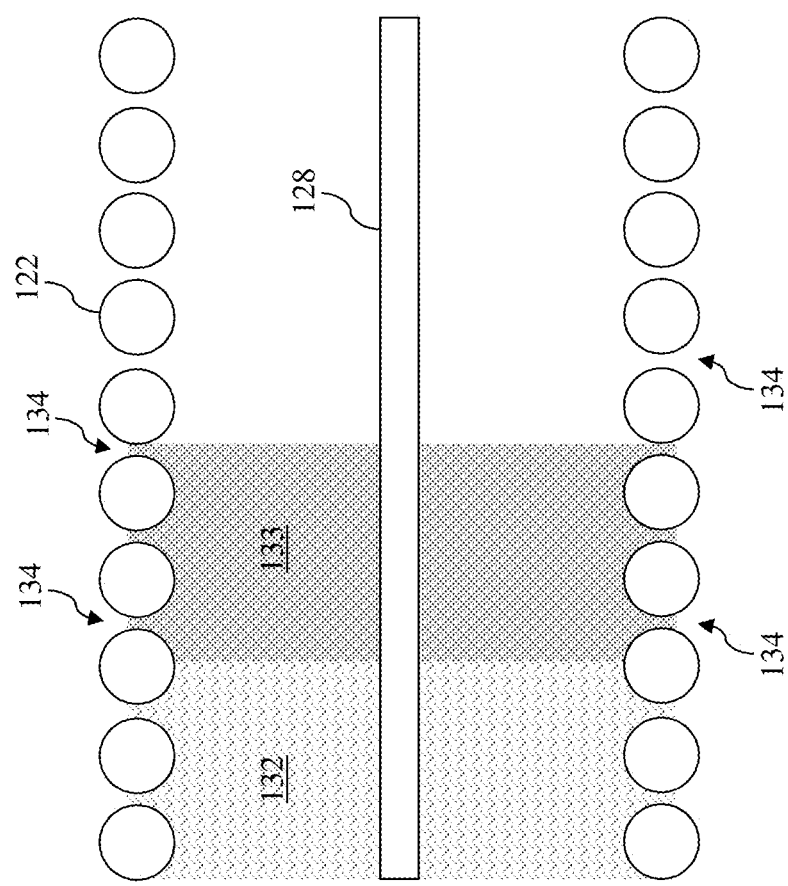
FIG. 6 is a magnified cross-sectional side view of a section of the distal portion of the intravascular device of FIGS. 1-3 according to yet another embodiment of the present disclosure.

Referring now to FIGS. 4-6, shown therein are magnified cross-sectional side views of the distal portion 104 of the intravascular device 100 according to various exemplary embodiments of the present disclosure. Referring initially to FIG. 4, a flexible adhesive 132 partially fills a central lumen of the distal flexible element 122. As shown, the flexible adhesive 132 at least partially fills spaces 134 between adjacent windings of the distal flexible element 122. In that regard, in some instances the flexible adhesive 132 is introduced into the central lumen of the distal flexible element 122 through the spaces 134 (e.g., by wicking, injecting, flowing, and/or combinations thereof). In some instances, the flexible adhesive 132 is introduced into the central lumen of the distal flexible element 122 through an opening in one of the ends of the flexible element 122 and filled until the material at least partially fills the spaces 134. In that regard, the flexible adhesive 132 is spaced from the outer most surface(s) 136 of the distal flexible element 122 in some embodiments.

As shown, the outer most surface(s) 136 of the distal flexible element 122 have a diameter 138. Generally, the diameter 138 is approximately equal to the maximum desired outer diameter of the intravascular device 100. Accordingly, in some particular implementations the diameter 138 is about 0.014", 0.018", or 0.035". The outer boundary 140 of the flexible adhesive 132 has a diameter 142 that is smaller than the diameter 138 of the distal flexible element 122 such that the material is spaced from the outer most surface(s) 136 of the distal flexible element. In some instances, the diameter 142 is less than the diameter 138 by between about 0.0001" and about 0.005", or other suitable range. Accordingly, in some instances, the diameter 142 is about 0.013", 0.017", or 0.034". In some implementations the diameter 142 is equal to the diameter 138 of the distal flexible element or reduced by up to two times the diameter of the tip coil wire utilized to form the coil. Accordingly, for a 0.014" outer diameter tip coil using 0.0025" diameter wire material, the diameter 142 may range from 0.009" to 0.014". Similarly, in some implementations, the diameter 142 is less than the diameter 138 by a percentage of the diameter of the wire material used to form the coil, such as ten percent, twenty percent, twenty-five percent, fifty percent or more the wire diameter.

By spacing the flexible adhesive 132 from the outer most surface(s) 136 of the distal flexible element 122, the tactile response to a user associated with the distal flexible element 122 contacting anatomical structures is maintained. On the other hand, if the flexible adhesive 132 completely covers the outer surface(s) of the distal flexible element 122, then a continuous surface of flexible adhesive 132 may be formed that can affect the tactile response of the intravascular device 100 when in use.

In the embodiment of FIG. 4, the flexible adhesive 132 extends along only a portion of the length of the distal flexible element 122. In particular, the flexible adhesive 132 is positioned only within a proximal section of the distal flexible element 122 such that a distal section of the distal flexible element 122 does not include the flexible adhesive. In that regard, the flexible adhesive 132 extends along the distal flexible element 122 between about 1 percent and about 100 percent of the length of the distal flexible element 122. In some instances, the distal flexible element 122 has a length of approximately 3 cm and the flexible adhesive 132 extends from a proximal end of the distal flexible element a distance between about 1 mm and about 20 mm. FIG. 5 illustrates another embodiment where the flexible adhesive 132 substantially fills the entire central lumen of the distal flexible element 122.

Referring now to FIG. 6, shown therein is another embodiment where multiple flexible adhesives are utilized within the distal flexible element 122. In particular, the flexible adhesive 132 fills a portion of the distal flexible element 122 and a flexible adhesive 133 fills another portion of the distal flexible element 122. In the illustrated embodiment, the flexible adhesive 133 is positioned distal of the flexible adhesive 132. In that regard, the relative material properties of the adhesives 132, 133 can be selected to provide a desired transition in stiffness along the length of the distal flexible element 122. For example, where the distal flexible element 122 extends from a rigid housing, it can be desirable to provide a gradual transition in stiffness from the housing to the distal flexible element 122. Accordingly, in some implementations the flexible adhesive 132 has an increased stiffness or durometer relative to the flexible adhesive 133 to facilitate a gradual transition in stiffness. The relative amounts of each adhesive 132, 133 utilized can be selected to achieve the desired stiffness transition along the length of the distal flexible element 122. Further, in some instances three or more adhesives having varying stiffness properties can be utilized.

Figure 7:
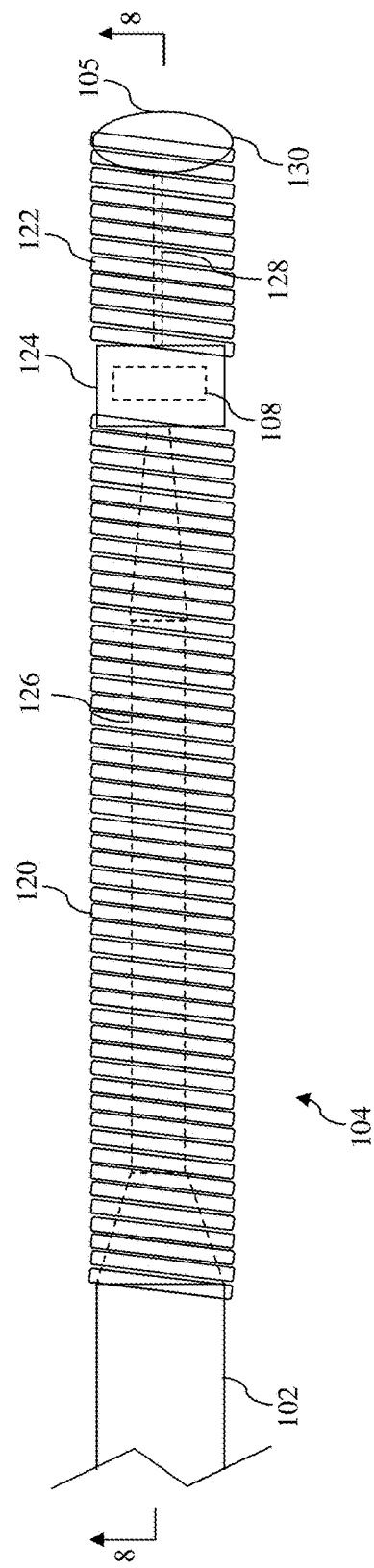
FIG. 7 a diagrammatic, schematic side view of a distal portion of an intravascular device according to another embodiment of the present disclosure.
Figure 8:
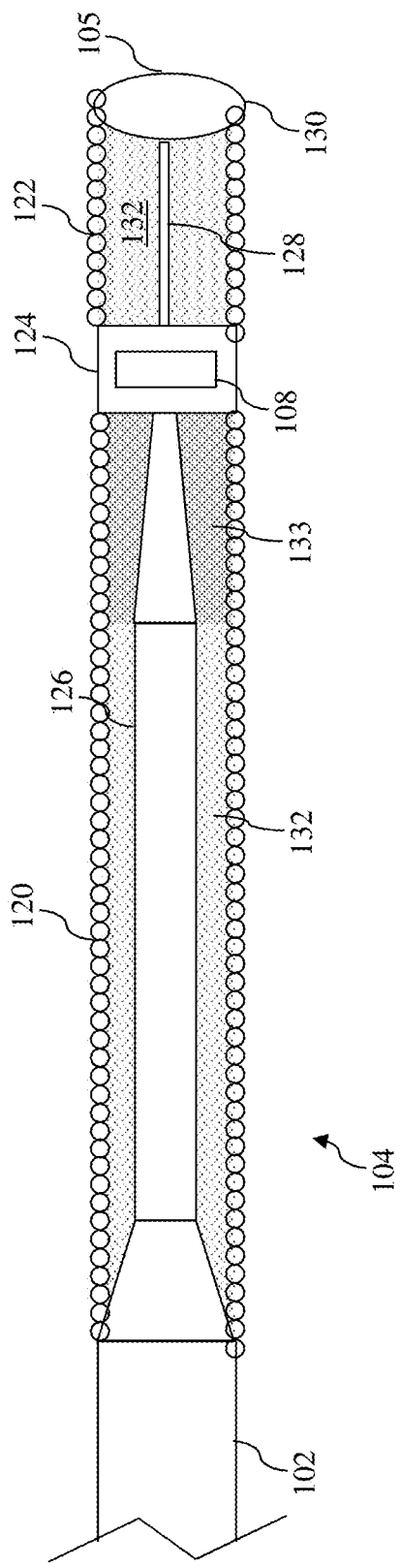
FIG. 8 is a cross-sectional side view of the distal portion of the intravascular device of FIG. 7 taken along section line 8-8 of FIG. 7 according to an embodiment of the present disclosure.

Referring now to FIGS. 7 and 8, shown therein is a diagrammatic, schematic side view of the distal portion 104 of the intravascular device 100 according to another embodiment of the present disclosure. As shown, the distal portion 104 includes a proximal flexible element 120 and a distal flexible element 122 on each side of a housing 124 containing component 108. Again, the proximal and distal flexible elements 120, 122 can be any suitable flexible element, including coils, polymer tubes, and/or coil-embedded polymer tubes. In the illustrated embodiment the proximal flexible element 120 is a coil and the distal flexible element 122 is a coil.

Referring now to FIG. 8, shown therein is a cross-sectional side view of the distal portion 104 of the intravascular device 100 taken along section line 8-8 of FIG. 7 according to an embodiment of the present disclosure. As shown, the proximal and distal flexible elements 120, 122 are filled, or partially filled, with one or more flexible materials. In that regard, the material(s) filling, or partially filling, the flexible elements is (are) configured to improve the mechanical integrity of the proximal and distal flexible elements 120,122, while maintaining sufficient flexibility for use of the intravascular device in tortuous vessels. In some instances, the materials include one or more flexible adhesives, such as Dymax 1901-M, Dymax 9001, etc. In that regard, in some implementations the flexible adhesives have a minimum durometer of shore hardness 25A to a maximum durometer of shore hardness 60D.

In the illustrated embodiment, the proximal flexible element 120 is filled with multiple types of flexible adhesives along its length. In particular, a flexible adhesive 132 fills a first portion of the proximal flexible element 120 and a flexible adhesive 133 fills a second portion of the proximal flexible element 120. In the illustrated embodiment, the flexible adhesive 132 fills a proximal section of the proximal flexible element 120 and the flexible adhesive 133 fills a distal section of the proximal flexible element 120 leading to the housing 124 and coinciding with a taper in the proximal core member 126. In that regard, the relative material properties and/or amounts of the adhesives 132, 133 can be selected to provide a desired transition in stiffness along the length of the proximal flexible element 122. Accordingly, in some implementations the flexible adhesive 132 has an increased stiffness or durometer relative to the flexible adhesive 133. Further, in some instances three or more adhesives having varying stiffness properties can be utilized along the length of the proximal flexible element 122.

In some instances, a method of forming or manufacturing a sensing guide wire in accordance with the present disclosure includes providing the requisite components and coupling them together in a manner to form the intravascular device 100. In that regard, the flexible element(s) can be filled, or partially filled, with the flexible adhesive(s) before and/or after coupling other components together. In that regard, the flexible adhesive(s) can be inserted into the flexible element(s) using any suitable techniques, including wicking, injecting, flowing, and/or combinations thereof. In that regard, in some instances the flexible adhesive(s) have a starting viscosity in the range of 10 CPS to 30,000 CPS, with some implementations being between about 200 CPS and 20,000 CPS. In some instances, the flexible adhesive(s) are UV cured with a secondary heat or moisture cure due to ensure any hidden sections are cured. However, the adhesive(s) can be heat and/or moisture cure only adhesives in some instances.

Figure 9:
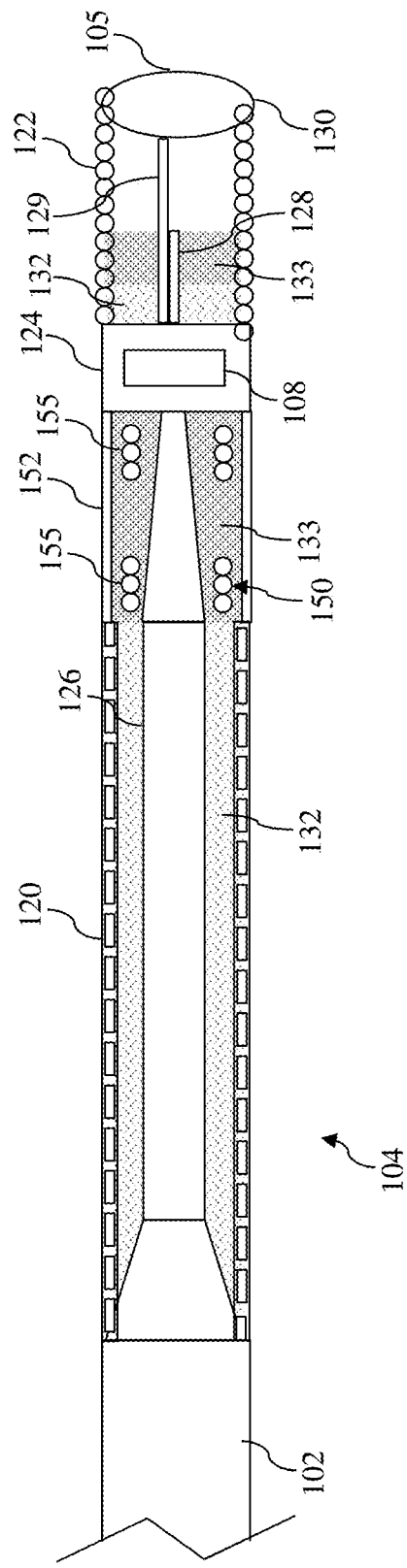
FIG. 9 is a cross-sectional side view of a distal portion of an intravascular device according to another embodiment of the present disclosure.
Figure 10:
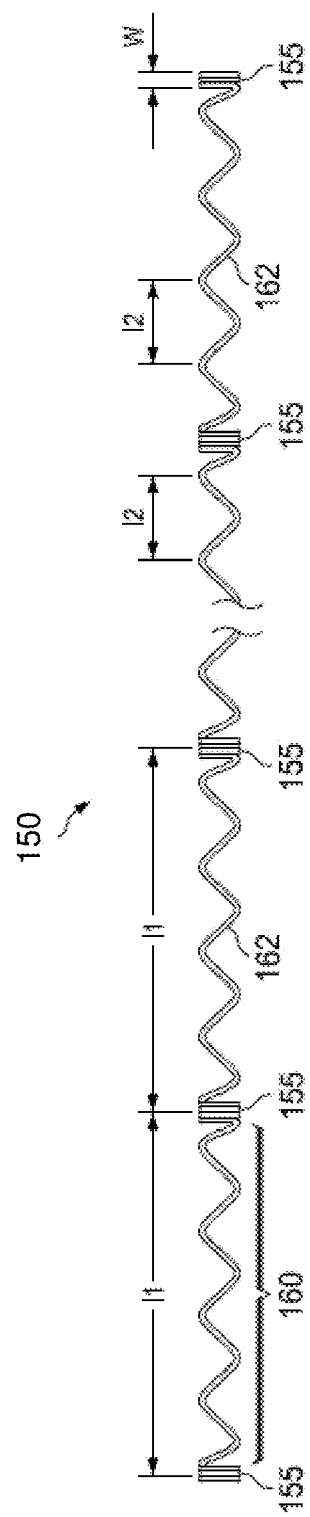
FIG. 10 is a side view of a variable pitch marker coil according to an embodiment of the present disclosure.

Referring now to FIGS. 9 and 10, shown therein are aspects of the distal portion of an intravascular device according to another embodiment of the present disclosure. In that regard, FIG. 9 shows a cross-sectional side view of the distal portion of an intravascular device similar to those of FIGS. 3 and 8 described above, but illustrating another embodiment. In particular, the distal portion 104 shown in FIG. 9 includes a proximal flexible element 120, a distal flexible element 122, and a housing 124 containing component 108. In the illustrated embodiment of FIG. 9, the proximal flexible element 120 includes a coil-embedded tube and the distal flexible element 122 is a coil. A core member 126 extends through the proximal flexible element 120 and the housing 124 such that a distal section of the core member 126 defines a core member 128 that extends through a portion of the distal flexible element 122. In that regard, the core member 128 is shown coupled to a shaping ribbon 129. In some implementations, the core member 128 is coupled to the shaping ribbon 129 utilizing a multi-flat transition as described in U.S. Provisional Patent Application No. 62/027,556, filed Jul. 22, 2014, which is hereby incorporated by reference in its entirety. In some embodiments where the distal flexible element 122 has a length of approximately 3 cm, the core member 128 extends along the length of the distal flexible element 122 approximately 2 cm such that only the shaping ribbon 129 extends the last 1 cm of the distal flexible element 122.

The distal portion 104 of the intravascular device 100 shown in FIG. 9 also includes a radiopaque marker element 150. In that regard, the radiopaque marker element 150 is formed of a variable pitch coil. For example, FIG. 10 illustrates an exemplary radiopaque marker element 150 having a variable pitch coil. In this embodiment, the radiopaque marker element 150 defines radiopaque markers in the form of tightly wound sections 155 separated by the loosely wound sections 162. The radiopaque marker element 150 may be formed of a single length of material that has been wound into areas of varying pitch and coated with a radiopaque material. Alternatively, the portions of the radiopaque marker element 150 that are to define the radiopaque markers can be formed of and/or coated with a radiopaque material. The radiopaque material may be one or more radiopaque metals including, but not limited to, gold, tungsten, iridium, rhodium, platinum, barium, bismuth, and combinations and/or alloys thereof. In some embodiments, the radiopaque material is a radiopaque polymer, which may comprise a matrix of a polymeric material in combination with a radiopaque metal. Any material with a high enough radiodensity when shaped into a tightly wound section 155 can be used. For example, the radiopaque marker element 150 may be formed of lower cost alternatives to precious metals with equivalent radiodensity.

The tightly wound sections 155 are tightly wound areas of the radiopaque marker element 150 that form blocks of greater radiopacity or radiodensity with respect to the loosely wound sections 162. As such, the tightly wound sections of the radiopaque element are ultrasonically recognizable to the imaging device. In some embodiments, the tightly wound sections 155 have a width (W) ranging from 1.0 mm to 5.0 mm. Both the tightly wound sections 155 and the loosely wound sections 162 retain the ability to flex. As a result, the tightly wound sections 155 may have greater widths W (and greater resultant visibility) than rigid, metallic marker bands without adversely affecting the flexibility of the intravascular device. Thus, the tightly wound sections 155 form flexible radiopaque markers that are capable of curving/bending with the intravascular device 100 as it traverses through tortuous anatomy without causing the inadvertent catheter kinking and/or trauma that can be caused by rigid marker bands. The coil winding process provides good control, allowing the creation of accurate marker configurations. In some instances, the tightly wound sections 155 are defined by a stack of coils. In that regard, the stack of coils may have slight spacing between each winding for improved bending performance through tortuous vessels.

The tightly wound sections 155 have a closed pitch while the loosely wound sections 162 have an open pitch. In other words, the tightly wound sections 155 are formed of tightly compressed individual coils having little to no space between them, while the loosely wound sections 162 are formed by coils having greater space between centers of adjacent coils 154. In some embodiments, the pitch of the coils in the loosely wound sections 162 may range from 1.1938 mm (0.047 inches) to 1.3462 mm (0.053 inches). In the pictured embodiment, the loosely wound sections 162 are formed by four loosely wound turns or coils. However, the loosely wound sections 152 may be formed by any number of turns or coils.

In one embodiment, the radiopaque marker element 150 is manufactured by stretching a tightly compressed coil at constant intervals past the recovery point of the coil material, thereby creating alternating areas of tightly wound coil and loosely wound coil. Stretching the coil past its recovery point "sets" the intervals between the individual coils and creates constant intervals between the tightly wound sections 155 and the loosely wound sections 162. For example, in the pictured embodiment in FIG. 10, the tightly wound sections 155 are separated from one another by a constant interval I1, which reflects a fixed distance between adjacent tightly wound sections 155. The individual coils of the loosely wound sections 162 are separated from one another by a constant interval I2, which reflects a fixed distance between adjacent loosely wound coils 154 in the loosely wound sections 152. The interval I1 may vary in different embodiments depending upon the particular application desired. For example, in various embodiments, the interval I1 may range from 0.5 cm to 5 cm.

In the illustrated embodiment of FIG. 9, the radiopaque marker element 150 is positioned within a polymer tube 152 and embedded in flexible adhesive 133 that serves to maintain the radiopaque marker element 150 in the desired spacing, while maintaining flexibility. In that regard, the flexible adhesive 133 serves to lock the coil configuration in the desired pattern and can eliminate the potential for movement of the coils during subsequent steps of the intravascular device manufacturing process, shipping, and use. In some embodiments, flexible adhesive 133 has an increased flexibility (i.e., lower durometer) than a flexible adhesive 132 filling a proximal section of the proximal flexible element 120. In some implementations, the flexible adhesive 133 is also used within a distal section of the proximal flexible element 120 such that there is continuity in the flexible adhesive across the boundary between the proximal flexible element 120 and the polymer tube 152.

The radiopaque marker element 150 allows co-registration of the location of the intravascular device 100 with other diagnostic techniques, such as external and internal imaging. For example, in some instances the radiopaque marker element 150 is utilized in combination with the housing 124 to define a pattern of radiopaque marker elements. For example, using the housing 124 and the tightly wound sections 155 of the radiopaque marker element 150 as markers and the loosely wound section 162 of the radiopaque marker element 150 as spacers, a repeating pattern of radiopaque markers with known spacings can be provided. The pattern of loosely and tightly wound sections of the radiopaque marker element 150 can be locked into place by use of the low durometer adhesive(s). Benefits of utilizing such an approach include: pressure wires having this patterned tip will be pushed past the lesion of interest and not get in the way of stent markers; can be utilized to identify the exact location of the sensor based on the location of the radiopaque housing; and use of various adhesive durometers can provide smooth transition to the housing even with use of the radiopaque marker element 150.

Figure 11:
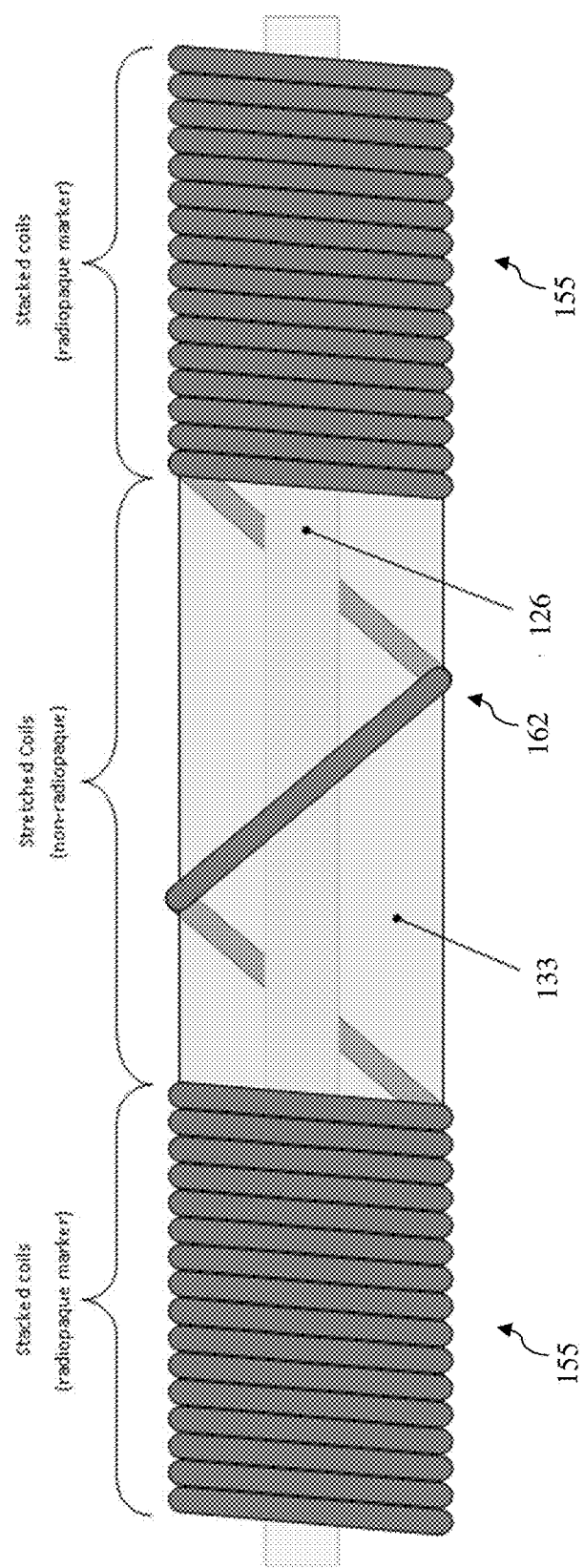
FIG. 11 is a side view of part of a distal portion of an intravascular device incorporating a variable pitch marker coil according to an embodiment of the present disclosure.

Referring now to FIG. 11, shown therein is another implementation of an intravascular device incorporating a radiopaque marker element. In particular, a section of a distal portion of the intravascular device is shown having a variable pitch radiopaque marker coil, including tightly wound sections 155 spaced by a loosely wound section 162. A flexible adhesive 133 is utilized to fill the loosely wound section 162. In that regard, in contrast to the embodiment of FIG. 9, in the embodiment of FIG. 11 the variable pitch radiopaque marker coil and/or the flexible adhesive 133 define the outer surface of the intravascular device. In other words, the radiopaque marker element is not positioned within polymer tube 152, or other surrounding structure. In such embodiments, the adhesive serves to lock the coils in the desired configuration to prevent unwanted movement during subsequent steps of the intravascular device manufacturing process, shipping, and use.

Figure 12:
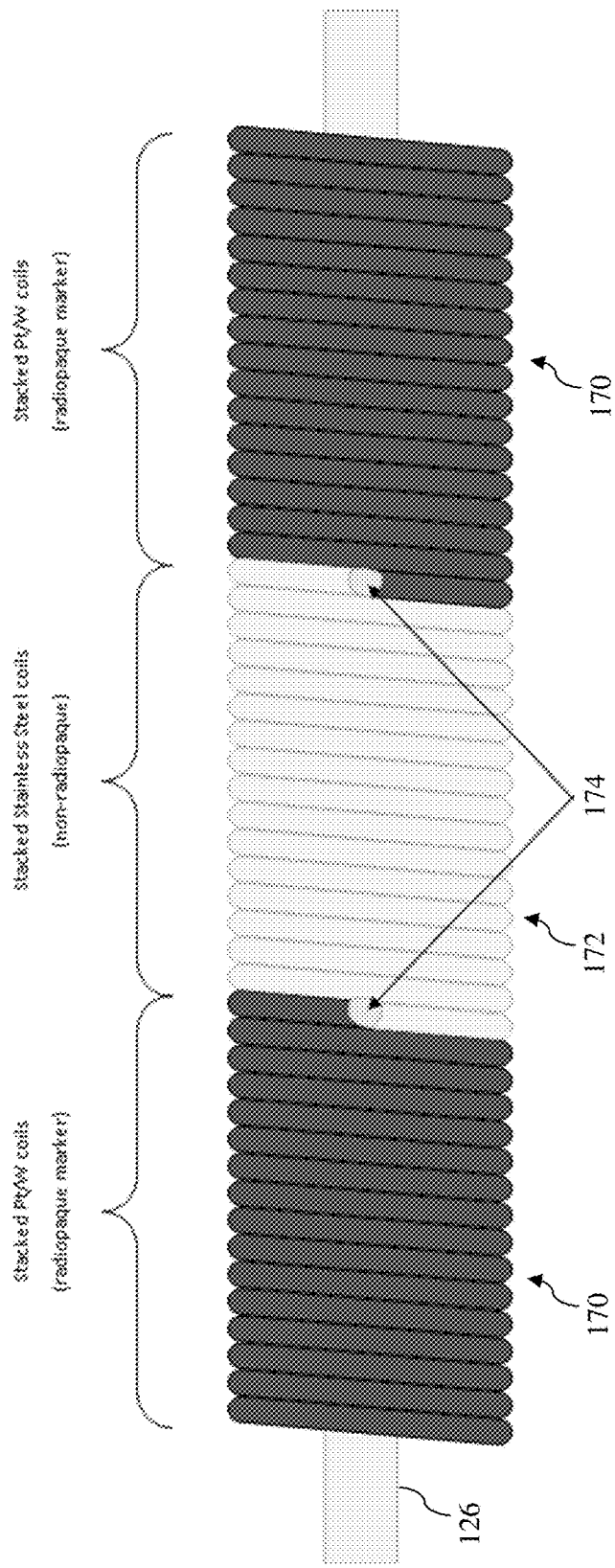
FIG. 12 is a side view of part of a distal portion of an intravascular device incorporating a varying radiopacity coils according to an embodiment of the present disclosure.

Referring now to FIG. 12, shown therein is another implementation of an intravascular device incorporating a radiopaque marker element. In particular, a section of a distal portion of the intravascular device is shown having radiopaque sections 170 spaced by a non-radiopaque (or at least less radiopaque) section 172. In the illustrated embodiment, the radiopaque sections 170 are defined by a stack of coils formed by and/or coated with a radiopaque material, while the non-radiopaque section 172 is formed by a non-radiopaque material (or at least a material less radiopaque than that forming sections 170). The radiopaque sections 170 are coupled to the non-radiopaque section 172 at weld points 174. In that regard, it is understood that additional welds beyond the end-to-end type weld shown in FIG. 12 may be used to achieve a desired coil alignment and/or tensile. In that regard, the separate coils can be assembled such that they perform similar to a coil wound as a single unit. Using such an approach, any pattern radiopaque and non-radiopaque sections is possible by choosing coils of desired lengths, though more markers require more welds. Further, such an approach provides a very distinct transition between the radiopaque and non-radiopaque sections. Further still, this multi-section approach can be used for the distal tip of the intravascular device that extends distally from a sensing element. In that regard, the need for markers proximal to a sensing element, which are often not desired by physicians, can be eliminated while still providing sufficient marker data to allow co-registration of the location of the intravascular device and, in particular, the sensing element. Further, a flexible adhesive may or may not be utilized to fill the radiopaque and/or non-radiopaque sections 170, 172.

Figure 13:
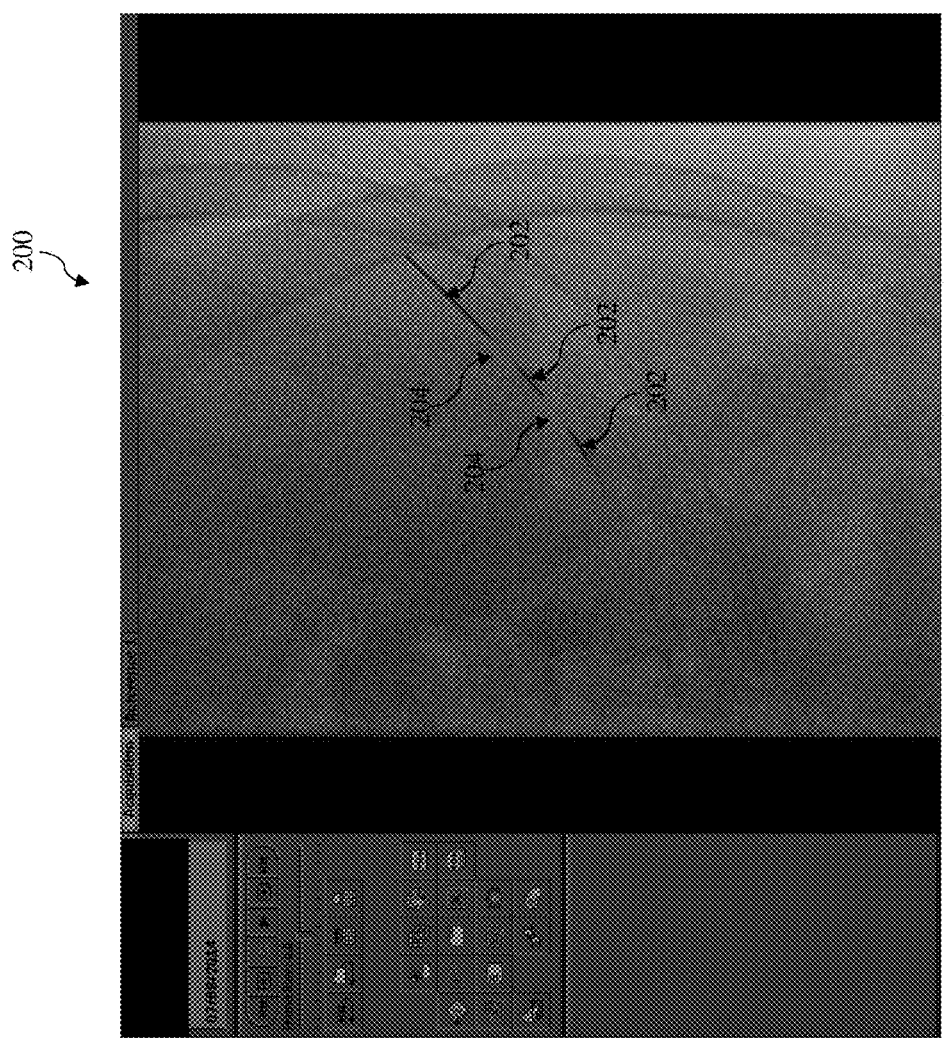
FIG. 13 is a fluoroscopic image of an intravascular device incorporating a variable radiopacity element according to an embodiment of the present disclosure.

Referring now to FIG. 13, shown therein is a fluoroscopic image 200 of an intravascular device incorporating a variable radiopacity element according to an embodiment of the present disclosure. The image 200 shows radiopaque sections 202 spaced by a non-radiopaque sections 204. In that regard, the radiopaque sections 202 are representative of the tightly wound sections 155 and/or the radiopaque sections 170 of FIGS. 9-12, while the non-radiopaque sections 204 are representative of the loosely wound sections 162 and/or the non-radiopaque sections 172 of FIGS. 9-12.

Guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
   a flexible elongate member;
   a flexible element positioned distal of the flexible elongate member and extending to a distal end of the sensing guide wire;
   a core member extending within a lumen of the flexible element;
   at least one flexible adhesive filling at least a portion of the lumen between the core member and the flexible element along a length of the flexible element;
   a sensor housing positioned proximal of the flexible element such that the at least one flexible adhesive and the flexible element extend distally from the sensor housing, wherein the sensor housing is more rigid than the at least one flexible adhesive; and
   a sensing element disposed within the sensor housing.

2. The guide wire of claim 1, wherein the sensing element includes at least one of a pressure sensor or a flow sensor.

3. The guide wire of claim 1, wherein the flexible element includes at least one of a coil, a polymer tubing, or a coil-embedded polymer tubing.

4. The guide wire of claim 1, wherein the at least one flexible adhesive includes a flexible adhesive selected from the group of adhesives consisting of urethane adhesives and silicone adhesives.

5. The guide wire of claim 1, wherein the at least one flexible adhesive includes a first flexible adhesive having a first durometer and a second flexible adhesive having a second durometer, the second durometer being less than the first durometer.

6. The guide wire of claim 5, wherein the second flexible adhesive is positioned distal of the first flexible adhesive.

7. The guide wire of claim 1, further comprising a radiopaque marker element positioned proximal of the sensing element.

8. The guide wire of claim 7, wherein the radiopaque marker element includes a variable pitch coil.

9. The guide wire of claim 8, wherein the variable pitch coil is embedded in the at least one flexible adhesive.

10. The guide wire of claim 7, further comprising a polymer sleeve surrounding the radiopaque marker element.

11. A sensing guide wire, comprising:
    a flexible elongate member;
    a radiopaque element positioned distal of the flexible elongate member, the radiopaque element being a variable pitch coil defining a first radiopaque section, a second radiopaque section, and a radiolucent section positioned between the first and second radiopaque sections;

a flexible element positioned distal of the radiopaque element and extending to a distal end of the sensing guide wire;

at least one flexible adhesive filling at least a portion of a lumen of the flexible element along a length of the flexible element; and a sensor housing positioned between the radiopaque element and the flexible element such that the at least one flexible adhesive and the flexible element extend distally from the sensor housing, wherein the sensor housing is more rigid than the at least one flexible adhesive; and a sensing element disposed within the sensor housing.

12. The guide wire of claim 11, wherein the first and second radiopaque sections are defined by tightly wound sections of the variable pitch coil and wherein the radiolucent section is defined by loosely wound section of the variable pitch coil.

13. The guide wire of claim 12, wherein the flexible adhesive fills at least the loosely wound section of the variable pitch coil.

14. The guide wire of claim 11, further comprising:

a proximal flexible element positioned proximal of the sensing element, wherein the flexible element comprises a distal flexible element positioned distal of the sensing element; and a second adhesive filling at least a portion of the lumen of the proximal flexible element along a length of the proximal flexible element.

15. The guide wire of claim 1, further comprising:

a proximal flexible element positioned proximal of the sensing element, wherein the core member extends within a lumen of the proximal flexible element, and wherein the flexible element comprises a distal flexible element positioned distal of the sensing element; and a second flexible adhesive filling at least a portion of the lumen of the proximal flexible element between the core member and the proximal flexible element along a length of the proximal flexible element.

16. The guide wire of claim 1, wherein the sensing guidewire comprises an outer diameter, and wherein the sensor housing defines the outer diameter for a portion of a length of the sensing guidewire.

17. The guidewire of claim 16, further comprising a proximal flexible element positioned around the core wire, wherein:

the flexible element comprises a distal flexible element positioned distal of the sensor housing, the sensor housing is positioned distal of a distal end of the proximal flexible element, and the sensor housing is positioned proximal of a proximal end of the flexible element.

* * * * *